US 6,635,216 B2

(12) United States Patent
Dundas et al.

(10) Patent No.: US 6,635,216 B2
(45) Date of Patent: Oct. 21, 2003

(54) BLOW MOLDING MACHINE AND METHOD (75) Inventors: Dennis L. Dundas, Dover, PA (US); Csaba M. Farkas, Dallastown, PA (US)

(73) Assignee: Graham Engineering Corporation, York, PA (US)

(*) Notice: Subject to any disclaimer, the term of this patent is extended or adjusted under 35 U.S.C. 154(b) by 253 days.

(21) Appl. No.: 09/861,315

(22) Filed: May 18, 2001

(65) Prior Publication Data

US 2002/0171179 A1 Nov. 21, 2002

(51) Int. Cl.⁷ .......................... B29C 49/46; B29C 49/58
(52) U.S. Cl. ................................. 264/525; 425/535
(58) Field of Search .......................... 425/535; 264/524, 264/525

(56) References Cited

U.S. PATENT DOCUMENTS

| 3,021,559 A | 2/1962 | Strong |
| 3,089,185 A | 5/1963 | Di Settembrini |
| 3,492,106 A | 1/1970 | Peters et al. |
| 3,694,424 A | 9/1972 | Hunkar et al. |
| 3,712,784 A | 1/1973 | Siard et al. |
| 3,717,429 A | 2/1973 | Peters et al. |
| 3,814,783 A | 6/1974 | Dardaine et al. |
| 3,819,317 A | 6/1974 | Higginbotham |
| 4,026,982 A | 5/1977 | Dardaine et al. |
| 4,150,689 A | 4/1979 | Britten |
| 4,173,447 A | 11/1979 | Bradbury ................... 425/526 |
| 4,208,852 A * | 6/1980 | Pioch ........................ 53/167 |
| 4,401,423 A | 8/1983 | Bellehache et al. ......... 425/210 |
| 4,617,077 A | 10/1986 | Giese et al. ................ 156/245 |
| 4,699,585 A | 10/1987 | Giese et al. ................ 425/522 |
| 4,880,581 A * | 11/1989 | Dastoli et al. ............... 264/39 |
| 4,946,366 A | 8/1990 | Dundas et al. ............. 425/536 |
| 4,948,356 A | 8/1990 | Dundas et al. ............. 425/522 |
| 4,950,153 A | 8/1990 | Dundas et al. ............. 425/536 |
| 5,022,544 A | 6/1991 | Dundas et al. ............... 215/31 |
| 5,037,684 A | 8/1991 | Dundas et al. ........... 428/36.92 |
| 5,068,075 A | 11/1991 | Dundas et al. ............. 264/505 |
| 5,085,822 A | 2/1992 | Uehara et al. ............. 264/528 |
| 5,182,122 A | 1/1993 | Uehara et al. ............. 425/526 |
| 5,622,735 A | 4/1997 | Krishnakumar et al. .... 425/530 |
| 5,759,218 A * | 6/1998 | Martin et al. .............. 55/385.1 |
| 5,795,533 A | 8/1998 | Mehnert .................... 264/529 |
| 5,851,479 A | 12/1998 | McGlynn et al. .......... 264/526 |
| 6,048,192 A | 4/2000 | McGlynn et al. .......... 425/536 |
| 6,214,282 B1 * | 4/2001 | Katou et al. ............... 264/524 |

FOREIGN PATENT DOCUMENTS

| DE | 2134166 | 1/1973 |
| DE | 3614229 A1 | 11/1987 |
| GB | 1296612 | 11/1972 |
| JP | 60-49919 | 3/1985 |

* cited by examiner

Primary Examiner—Robert Davis
(74) Attorney, Agent, or Firm—Hooker & Habib, P.C.

(57) ABSTRACT

A blow molding machine and method for blowing sealed aseptic bottles includes a blow pin having separate blow air and exhaust passages. The retracted blow pin is dwelled in a pin housing filled with sterile air. The housing is connected to the pin by two thin rolling diaphragm seals. Sterile air in the chamber maintains the sterility of the sides and end of the blow pin. The separate blown air and exhaust passages maintain sterility of the machine despite possible rupture of a parison or bottle.

34 Claims, 4 Drawing Sheets

BLOW MOLDING MACHINE AND METHOD

FIELD OF THE INVENTION

The invention relates to a blow molding machine and method for blow molding and sealing aseptic bottles, which, subsequent to molding, are opened and filled without the necessity of sterilization before filling.

DESCRIPTION OF THE PRIOR ART

In order to blow mold sterile bottles it is necessary to sterilize all tooling which contacts and may contaminate the interior of the parison or bottle. It is difficult to maintain the sterility of a blow pin used in shuttle blow molding because of the large size and blunt shape of the pin and the necessity of extending the pin a relatively long distance into the neck recess of a closed blow mold.

During blow molding of aseptic bottles sealed closed in the molds, it is necessary to first blow the bottle and then to reduce the interior pressure to below atmospheric pressure prior to sealing the bottle. This is because the blown bottles contain hot plastic which gives off residual heat during cooling. This heat warms the gas in the sealed bottle to increase the pressure in the sealed bottle.

The plastic in the bottle stabilizes in a permanent shape long after the bottle is removed from the mold. When the bottle is sealed closed at atmospheric pressure the gas in the bottle is warmed and increases the pressure in the bottle above atmospheric pressure to bow the walls of the bottle outwardly prior to stabilization of the plastic. The plastic bottle then stabilizes with undesired bowed walls or bottom. Reducing the interior pressure of a sealed aseptic plastic bottle blown using a blow needle is explained in U.S. Pat. No. 5,037,684, the disclosure of which is incorporated herein by reference in its entirety.

The pressure of the air in the aseptic bottle must be reduced below atmospheric pressure before the bottle is sealed. Blow air is conventionally withdrawn through the same passage used to flow blow air into the bottle. Exhaustion of blow air from the bottle through a common blow exhaust passage incurs the risk that rupture of the parison or bottle will result in drawing of nonsterile atmospheric air through the blow passage while removing blow air and will contaminate the passage. When the blow passage is contaminated subsequently blown bottles may be contaminated. The blow molding machine must be shut down and resterilized before manufacture of aseptic bottles can recommence. This is a lengthy and time-consuming process.

Accordingly, there is a need for an improved shuttle blow molding machine and method for blow molding sealed aseptic plastic bottles, which maintains the sterility of the blow pin and the blow passage during operation of the machine. Additionally, the machine should assure that rupture of a parison or bottle does not result in atmospheric air being withdrawn through the blow tube, which requires resterilization of the machine.

SUMMARY OF THE INVENTION

The invention is a blow molding machine with an improved blow pin assembly and method for shuttle blow molding to blow and seal aseptic bottles having a desired shape and which, when opened, are sterile and ready for filling. The machine maintains the sterility of the blow pin by surrounding the pin with sterile air and flowing the sterile air along the length of the pin in a laminar, circumferential flow extending around the blunt end of the pin. The laminar flow of sterile air adheres to the sides of the pin and, due to the Coanda effect, flows around the end of the pin to completely surround the end of the pin with sterile air and shield the pin from contaminated air.

After molding, the blow pin is retracted into a sterile chamber in a blow pin housing. The housing is connected to the pin by two narrow and easily flexed rolling diaphragm seals. The rolling diaphragm seals provide redundant protection against contamination of the blow pin chamber from unsterilized atmospheric air. A low-pressure chamber between the two seals increases the useful life of the seals and maintains sterility of the sterile chamber in the unlikely event the seals leak. The differential pressure across each seal assures that during blow pin extension and retraction the seals properly contact the adjacent surfaces of the housing and pin and do not wrinkle.

During blowing, high pressure blow air is flowed through a blow passage in the pin and into a parison held in a closed mold cavity. The air expands the molten parison to blow the bottle. After blowing, the blow air is exhausted from the blow cavity through an exhaust passage separate from the blow passage. The pressure in the blown bottle is reduced below atmospheric pressure prior to sealing the bottle closed. In this way, the bottle will assume the proper shape when the plastic in the bottle is fully stabilized. The provision of a separate exhaust passage for withdrawing blow air from the interior of the bottle assures that no exhaust air flows through the blow passage. This is important in the event a parison or bottle accidentally ruptures or is not properly captured by the mold, permitting flow of atmospheric air into the bottle or parison and out through the blow pin. Atmospheric air withdrawn through the exhaust passage may contain contaminants, which would destroy the sterility of this passage. However, such contamination would not destroy the sterility of the blow passage and would not prevent the machine from blowing sealed aseptic bottles. After the ruptured parison or bottle is ejected, the machine continues to blow sealing aseptic bottles as before, without the need for resterilization.

Other objects and features of the invention will become apparent as the description proceeds, especially when taken in conjunction with the accompanying drawings illustrating the invention, of which there are four sheets and one embodiment.

DESCRIPTION OF THE PREFERRED EMBODIMENT

Shuttle blow molding machine 10 includes two part mold 12 defining a plurality of cavities 14 for blow molding bottles when closed and a mold shift drive for shuttling the mold between a parison station where a parison is extruded down into the open mold for each mold cavity and blow station 16 where parisons captured in the mold cavities are blown to form aseptic bottles and are sealed closed to maintain sterility. The machine also includes a drive for opening and closing the molds. The mold shift drive and the opening and closing drive are conventional and are not illustrated.

Figure 1:
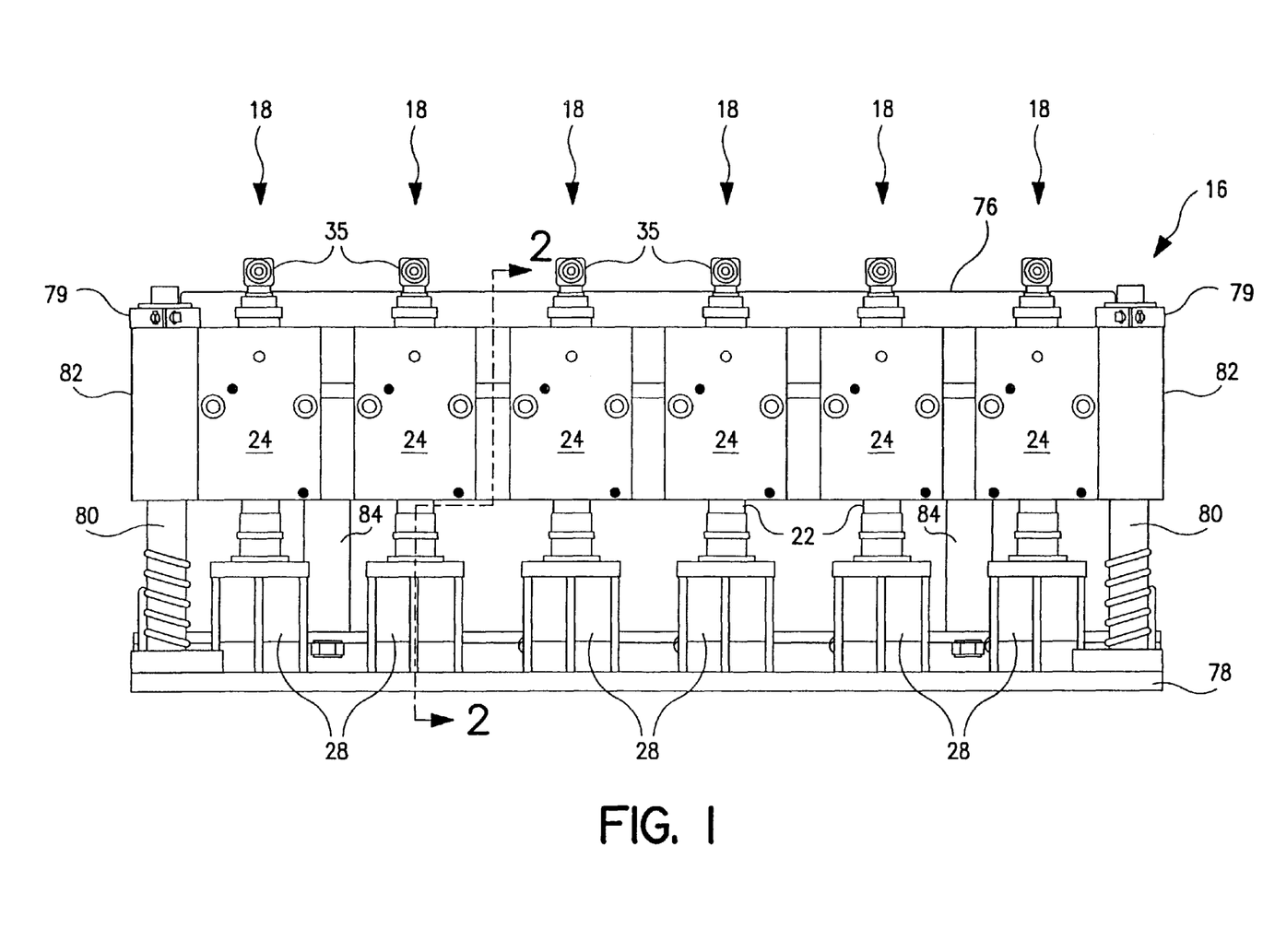
FIG. 1 is a front view of blow pin assemblies mounted at a blow station of a shuttle type blow molding machine.

FIG. 1 illustrates a number of blow pin assemblies 18 at blow station 16. Each blow pin assembly 18 is located above a mold cavity 14 and a captured parison 20 in the cavity when the mold is at the blow station.

Each assembly 18 includes an elongate blow pin 22 having an upper end mounted in a block 24 and a lower end 26 extending through the center of a blow pin housing 28. The blow pin is moveable axially relative to the housing from a retracted dwell position shown in FIG. 2 where pin end 26 is located in sterile annular chamber 30 and an extended blow position shown in FIG. 4 where the end 26 of the pin projects below the housing. The blow pin 22 includes an axial blow air tube 32 having a lower end forming a discharge mouth 34 at the lower end 26 of the blow pin. Tube 32 forms a blow air passage extending from a source of high-pressure, sterile blow air (not illustrated) through a control valve (not illustrated) and blow air inlet port 35 on block 24 to the upper end of tube 32. Mouth 34 is recessed a short distance into the end of the blow pin to prevent contamination of the tube by contact with a non-sterile object. Contact could occur during setup, maintenance or modification of the blow molding machine.

An annular discharge passage 36 surrounds tube 32 in the blow pin and extends from annular inlet 38, surrounding mouth 34 of tube 32 at the lower of the blow pin, along the length of the pin to block 24. The upper end of passage 36 is connected to a low-pressure vacuum port (not illustrated) which is connected to a low-pressure vacuum source (not illustrated) through a control valve (not illustrated).

Blow pin housing 28 includes lower cylindrical member 40 defining lower mouth 42, central cylindrical member 44 and upper cylindrical member 46 defining an upper opening 47. The three members 40, 44 and 46 are clamped together by a plurality of through bolts 48 engaging members 40 and 46. Blow pin 22 includes a cylindrical member 50 positioned adjacent central housing member 44 and moveable with the blow pin up and down relative to member 44. Member 50 is held in place on the blow pin between cylindrical upper and lower clamps 52 and 54.

Figure 2:
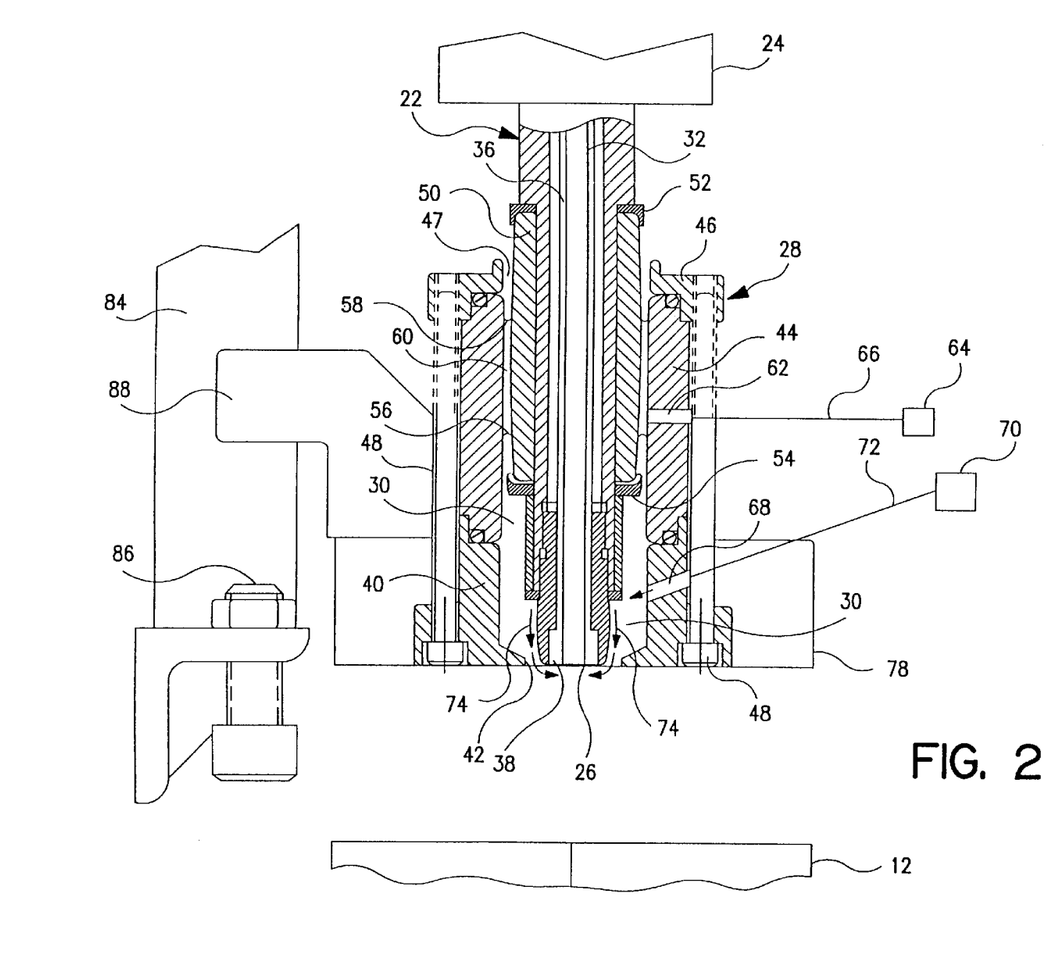
FIG. 2 is a side view, partially broken away, taken generally along line 2—2 of FIG. 1.

Two impermeable rolling diaphragms 56 and 58 extend between housing 28 and the blow pin to seal the upper end of chamber 30 from atmospheric air outside the assembly and pin. As illustrated in FIG. 2, the outer circumferential edge of diaphragm 56 is clamped in a circumferential recess between housing members 40 and 44 and the inner circumferential edge of diaphragm 56 is clamped between member 50 and lower clamp 54. The outer circumferential edge of seal 58 is clamped in a circumferential recess between members 44 and 46 and the inner circumferential edge of seal 58 is clamped between member 50 and upper clamp member 52.

Each diaphragm 56, 58 includes a unshaped circumferential seal which contacts the inner surface of member 44 and the outer surface of member 50 and rolls along the surfaces as pin 22 moves relative to the housing 28. The 180 degree bends in the seals face each other and the portions of the seals engaging members 44 and 50 extend away from the 180 degree bends.

The two diaphragm seals 56 and 58, the interior surface of member 44 and the exterior surface of member 60 between the seals define a closed annular chamber 60 between the blow pin and housing. Sterile air inlet port 62 in central member 44 communicates chamber 60 with vacuum source 64 through vacuum line 66. Source 64 maintains chamber 60 below atmospheric pressure to assure that there is a pressure differential extending across each of the diaphragm seals. The differential pressure maintains flush engagement between the seals and the surfaces of members 44 and 50 during extension and retraction of the blow pin. The upper and lower inner surfaces of member 50 are tapered slightly to facilitate flush engagement with the diaphragm seals. Seals 56 and 58 are very flat and occupy little radial space. The diaphragm seals are easily flexed and do not exert high loading forces on the blow pin assembly. Other types of seals or even a single seal may be used, if desired.

Figure 4:
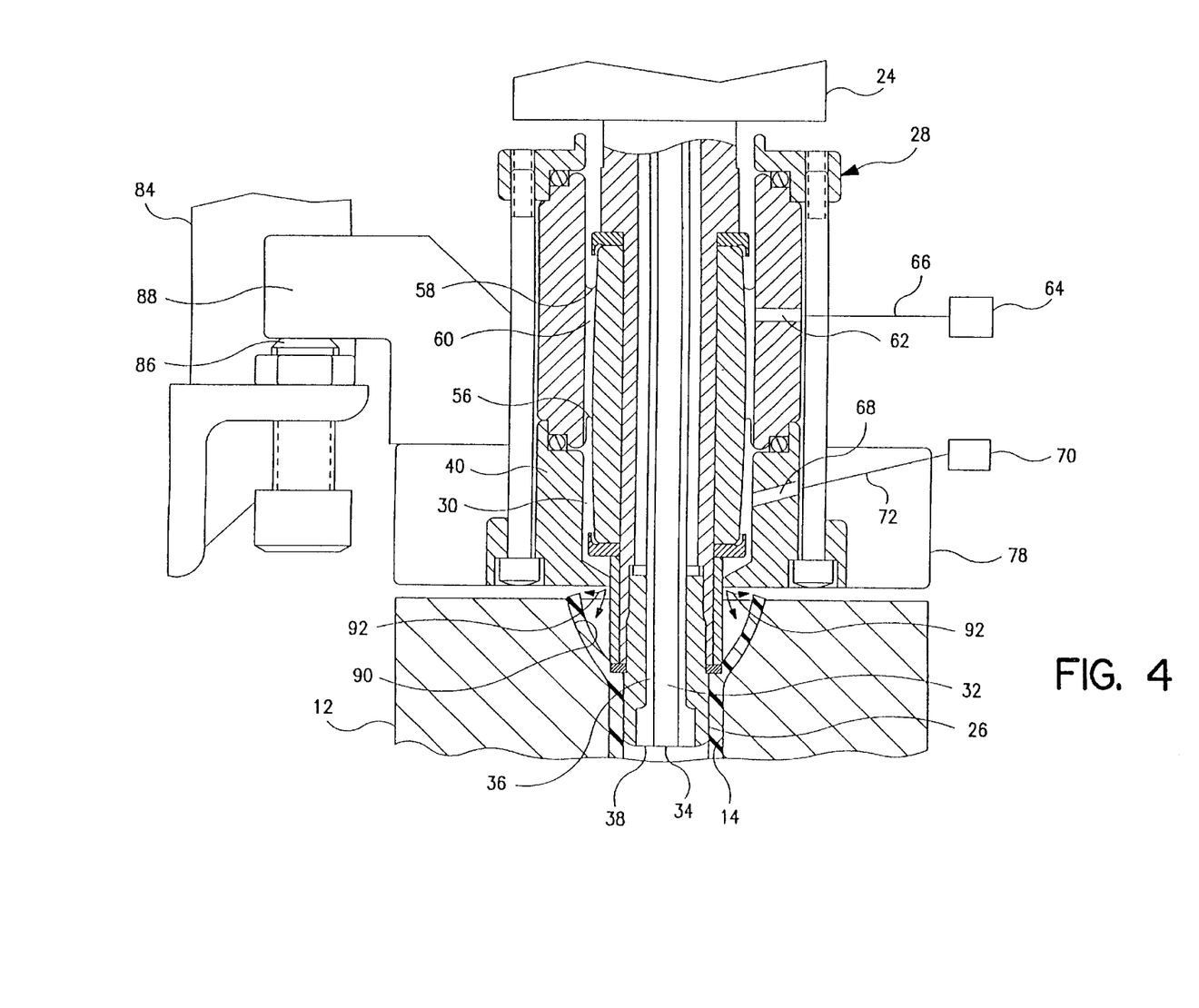

When blow pin 22 is retracted as shown in FIG. 2, the lower end of the pin is located in chamber 30. Opening 68 is formed in member 40 and is connected to a source of low-pressure sterile air 70 through line 72. Sterile air is continuously flowed through passage 68 to chamber 30. The sterile air surrounds the blow pin and flows axially along the blow pin in laminar flow and out the circular opening between the lower end of the blow pin and mouth 42. The sterile laminar flow adheres to the pin and, due to the Coanda effect, is drawn over the downwardly facing end of the blow pin to prevent atmospheric air from contaminating the pin. In this way, sterile air supplied through passage 68 protects the retracted blow pin from contamination by unsterile atmospheric air. Sterile air is flowed in chamber 30 when the pin is extended as shown in FIG. 4. The diameter of the pin is slightly less than the diameter of mouth 42, permitting sterile air from chamber 30 to flow down along the circumference of the extended pin and into the top of mold cavity 14 as illustrated. This flow protects the extended blow pin from contamination.

Block 24 in each assembly 18 is mounted on horizontal support block 76. Blow pin housings 28 are mounted on horizontal plate 78, which is supported by two upwardly extending guideposts 80 at the ends of the plate. The posts 80 extend through sleeve bearings 82 mounted on block 76 to permit vertical movement of plate 78 relative to block 76. Collars 79 on posts 80 prevent movement of plate 78 below the position of FIG. 1. Two fixed, vertical posts 84 support adjustable stop members 86, shown in FIGS. 2–4. A pair of stop fingers 88 on plate 78 engage stop members 86 to limit downward movement of the plate and blow pin housings 28 relative to block 76 and blocks 24. Gravity normally holds plate 78 below block 76 with collars 79 engaging bearings as shown in FIG. 1.

A suitable blow pin drive (not illustrated) lowers and raises block 76 to move the blow pin assemblies 18 down toward the two-part mold 12 and to withdraw blow pin assemblies up from the mold. During lowering, fingers 88 engage stops 86 with the blow pins withdrawn in chambers 30 and plate 78 a short distance above the mold. Continued lowering of block 76 and blocks 24 extends the blow pins into the neck portions 90 of the mold cavities to engage the parisons prior to blow molding, as shown in FIG. 4.

During startup of machine 10 chambers 30, the surfaces of the blow pins located below rolling diaphragm seals 56, all blow air passages including the blow tubes 32, exhaust passages 36, 68 and lines 72 are sterilized using high temperature steam. After initial sterilization, sterile air at a pressure less than one pound per square inch is flowed from source 70 through lines 72 into chambers 30. The low pressure sterile air completely fills the chambers below seals 56 and establishes laminar axial flows of sterile air along the ends of the retracted blow pins and out through mouths 42. Low pressure air is required in order to achieve the desired laminar flow along the blow pin. Higher pressure air would create turbulent flow. Due to the Coanda effect, sterile air is drawn across the exposed ends of the pins over mouths 34 of the blow tubes 32 and mouths 38 of exhaust passages 36. The continuous flow of sterile air into chambers 30 and around, along and over the ends of the retracted blow pins maintains the sterility of the blow pins by preventing atmospheric air, which may contain non-sterile contaminants, from contacting the retracted blow pin. Sterile air fills chambers 30 at a positive pressure. During the interval the blow pins are extended, sterile air flows out from chambers 30 through 0.02 inch clearances between each side of the pin and mouth, as indicated by arrows 92 in FIG. 4. This flow protects the extended pin from contamination.

A cycle of operation of blow molding machine 10 will now be described.

The cycle starts with the open mold 12 at the extrusion station and with parison extruders located above each open mold cavity extruding a parison down between the mold halves. The molds close over the parisons to capture each parison in a cavity. The captured parisons are severed from the remainders of the parisons and the closed mold is shifted to blow station 16 with each closed cavity and parison located under a blow pin assembly 18. Assemblies 18 are in the elevated position as shown in FIG. 2 with fingers 88 above stop members 86.

Next, the blow pin drive lowers block 76 to move the blow pins, plate 78 and pin housings 28 toward closed mold 12. Plate 78 and housings 28 are lowered with the blow pins until fingers 88 engage stops 86. This engagement stops lowering of plate 78 a short distance above the top of the closed mold 12. Further lowering of support block 76 extends the blow pins outwardly from chambers 30 and down into the neck portions 90 of the mold cavities. FIG. 4 illustrates the position with plate 78 fully lowered, fingers 88 engaging stops 86 and the blow pins fully extended. Lower ends of the pins seal the parisons at the upper portions of the mold cavities. Blow tube mouths 34 and exhaust passages 38 open into the captured parisons.

Blow air is then flowed through blow tubes 32 and into the interior of the parisons to expand the molten parisons outwardly and form bottles having a shape defined by the shape of the mold cavities. The blow air, which may have a pressure of about 88 pounds per square inch, holds the molten parisons against the walls of the cavities. The molds extract heat from the molten plastic so that the plastic quickly sets to form bottles. However, relatively large bodies of plastic at the bottom of the bottles remains molten after the remainder of the bottles are set. This plastic releases heat during cooling, prior to stabilization of the plastic.

After the bottle is blown and set, a valve between the source of blow air and blow tubes 34 is closed and a valve in the line connecting ports 39 to a source of subatmospheric air, which may be at a pressure of about −7 PSI, is opened to extract blow air from the interior of the bottle. The exhaust passages 36 are connected to the source of low-pressure air for a period sufficient to reduce the pressure in the bottles to a desired pressure below atmospheric pressure. When this occurs, the mold opens and shuttles back to the extrusion station leaving the bottles suspended on the blow pins. Sealing tooling located in masking arms below the extended blow pins and above the necks of the bottles close to seal the interiors of the bottles as the arms grip the bottles. The plastic adjacent the sealing tooling is kept hot to facilitate sealing. The sealing tooling may be of the type shown in U.S. Pat. No. 5,037,684. The negative pressure applied to exhaust passages 36 is deactivated after the bottles are sealed.

Figure 3:
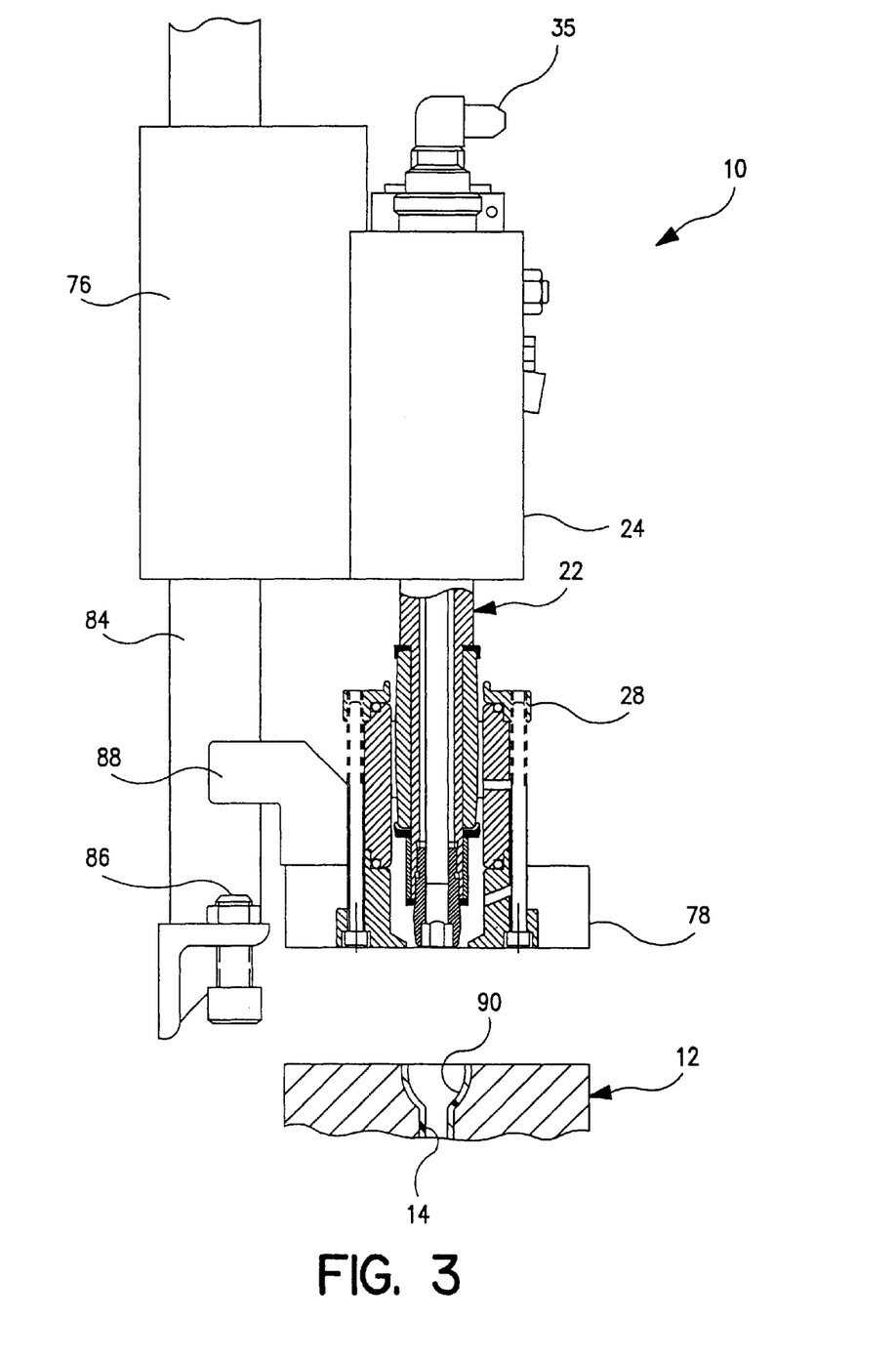
FIGS. 3 and 4 are views like FIG. 2 illustrating operation of the blow molding machine at the blow station.

After the bottle is sealed closed at a subatmospheric pressure the masking arms hold the bottles and the blow pin drive lifts block 76 up to extract the blow pins from the tops of the bottles and return the blow pin assemblies to the start position shown in FIGS. 1–3. The arms transfer the bottle from the machine.

During the time the blow pins are extended into the molds sterile air continues to be flowed into chamber 30 and out of the chamber through the narrow gap between the blow pin and chamber mouth 42. This air floods the exposed blow pins to prevent atmospheric air from contaminating the blow pins. Additionally, the high temperature of the molten plastic in the parison, about 400 degrees F., assists in maintaining sterility of the blow pin by heating the surface of the pin above a sterilizing temperature.

The set bottles withdrawn from the mold cavities contain bodies of molten or near molten plastic. These bodies gradually cool and release heat, which heats the subatmospheric air in the bottle and increases the pressure of the air in the bottle. When the latent heat is fully released from the plastic bodies the pressure in the bottle has been increased substantially to atmospheric pressure so that there is no significant pressure differential across the walls of the bottle and the bottle is in its desired molded shape when the plastic in the bottle stabilizes. Blowing of aseptic plastic bottles which are sealed at subatmospheric pressure to avoid deformation of the bottle when fully stabilized is more fully explained in U.S. Pat. No. 5,037,684.

After the bottles are removed from the open mold, the mold is moved back to the parison station to complete the cycle of operation of molding machine 10.

Exhaust passage 36 is maintained at a negative pressure during evacuation of the bottle until the bottle is sealed closed at the desired negative pressure. The exhaust passage is separate from the blow passage so that exhaust air does not flow through the sterile blow passage. This is important in the case a ruptured parison or bottle is blow molded and permits contaminated air to flow into the bottle or parison through the rupture. This air may contain contaminants and is withdrawn through exhaust passage 36. Contaminants in the exhaust air can render the exhaust passage nonsterile. Contaminates, however, cannot enter blow tube 32 because during exhaustion of blow gas exhaust passage 36 is maintained at a pressure lower than the pressure in the blow tube. This assures that a ruptured bottle does not destroy the sterility of the blow pin. Contaminants in the blow passage could destroy sterility of the bottles.

During mold changeover, and modification or adjustment of the molding machine the sterility of retracted blow pins may be maintained by continuing to flow sterile air from source 70 into chambers 30 and around the blow pins and out the chamber as previously described. Maintenance of the sterile flow of air around the blow pins permits startup of the machine after a mold change, adjustment or modification without the necessity to resterilize the pin assemblies. The lower ends of the blow tubes are located short distances above the bottom of the blow pins to further protect the sterility of the tubes.

Use of two rolling diaphragm seals 56 and 58 with a vacuum chamber 60 between the seals provides redundant protection of sterile chamber 30 from contamination by atmospheric air. A leak through the lower blowing diaphragm seal 56 could result in sterile air from chamber 30 flowing into the low-pressure chamber 60. This air would be drawn away from the machine to low pressure source 64 without contamination. A leak through the upper rolling diaphragm seal 58 would result in the flow of atmospheric air into the low-pressure chamber 60. Such flow, however, would likewise be drawn away to low-pressure source 64 without jeopardizing the sterility of chamber 30. In the unlikely event of small leaks of both seals 56, 58 air flowing through both ruptures would be drawn into low-pressure chamber 60 and safely away to low-pressure source 64 without contamination of chamber 30.

The blow pins are maintained sterile by flowing sterile air into the blow pin housings, along the pins and around and ends of the pins. Obviously, the blow pins could be maintain sterile by flowing a sterile gas other than air into the housings and around the pins as described.

While we have illustrated and described preferred embodiments of our invention, it is understood that this is capable of modification, and we therefore do not wish to be limited to the precise details set forth, but desire to avail ourselves of such changes and alterations as fall within the purview of the following claims.

What we claim as our invention:

1. A blow pin assembly for use in blow molding aseptic plastic bottles, the assembly including:
   A) an elongate blow pin having a blow end, the pin including a sterile internal blow air passage extending along the pin and having a blow mouth at the blow end of the pin;
   B) an annular blow pin housing surrounding the blow pin, the housing defining an upper opening and a lower mouth, and a sterile gas inlet port opening into a first annular chamber between the housing and the blow pin;
   C) a first circumferential seal adjacent the upper opening, said first seal extending between the housing and the blow pin, said seal closing the top of the chamber and permitting axial movement of the blow pin relative to the housing between a retracted position where the blow end of the pin is adjacent the housing and an extended position where the blow end of the pin is extended outwardly below the housing in position to blow a parison held in a closed mold below the housing, the surface of the pin below the first seal being sterile; and
   D) a drive for moving the blow pin between the retracted and extended positions;
   E) wherein when the blow pin is in the retracted position sterile gas flowed into the chamber through the sterile gas inlet port at low pressure surrounds the blow pin, flows along the blow pin in laminar flow and across the blow end of the pin to shield the sterile pin from contamination by atmospheric air.

2. The assembly as in claim 1 including a circumferential clearance between the blow pin and the mouth of the housing when the blow pin is in the extended position wherein sterile gas from the chamber flows through the clearance and around the extended blow pin to shield the pin from contamination by atmospheric air.

3. The assembly as in claim 1 wherein the first circumferential seal includes a first circumferential portion mounted on the blow pin, a second circumferential portion mounted on the housing and a circumferential flexible portion extending between said first and second portions.

4. The assembly as in claim 3 wherein said flexible portion comprises a diaphragm.

5. The assembly as in claim 4 wherein the diaphragm includes a circumferential bend.

6. The assembly as in claim 5 wherein said bend is located between two circumferential diaphragm portions, such portions extending away from said bend in the same direction.

7. The assembly as in claim 6 wherein said diaphragm portions contact the blow pin and housing, respectively.

8. The assembly as in claim 1 wherein the first seal comprises a first flexible diaphragm, and including a second seal extending between the housing and the blow pin and including a second flexible diaphragm, said second seal spaced a distance along the pin from the first seal, a second annular chamber located between said seals, the blow pin and the housing; and a vacuum port opening into said second annular chamber wherein a source of vacuum connected to the vacuum port maintains the second annular chamber at subatmospheric pressure.

9. The assembly as in claim 1 wherein the blow pin includes an exhaust passage separate from the blow passage, the exhaust passage extending along the pin and having an exhaust mouth at the blow end of the pin adjacent the blow mouth, wherein when the blow pin is in the extended position sterile blow air is flowed into a parison through the sterile blow tube to blow the parison and, after blowing of the parison, blow air is exhausted from the bottle through the exhaust passage only to prevent contamination of the sterile blow tube by contaminated air flowing into the parison or bottle due to a rupture.

10. The assembly as in claim 1 wherein the blow tube mouth is recessed in the end of the blow pin.

11. The assembly as in claim 1 including a source of sterile gas at a pressure of about one pound per square inch and a gas line connecting the source to the sterile gas to the inlet port wherein sterile gas at said pressure is flowed through the port into the chamber, around and along the blow pin.

12. A blow pin assembly for blowing aseptic plastic bottles, the assembly including:
   A) an elongate blow pin having a blow end, a sterile blow passage located in the blow pin and extending along the pin to a blow mouth at the blow end of the pin, and an exhaust passage located in the blow pin and extending along the blow pin to an exhaust mouth at the blow end of the blow pin, the exhaust mouth located adjacent to the blow mouth, the exterior surface of said pin being sterile from the blow end a distance along the pin away from the blow end;
   B) a blow pin sterilization maintenance device surrounding the blow pin to maintain the sterility of the surface of the blow pin;
   C) a blow pin drive for axially extending and retracting the blow pin to move the blow pin between a retracted position with the sterile surface of the pin located adjacent the sterilization maintenance device and an extended blow position with the end of the blow pin located away from the sterilization maintenance device for engagement with a parison held in a blow mold cavity;
   D) a first source of sterile blow gas connected to the blow passage of the blow pin away from the blow end; and
   E) a vacuum source connected to the exhaust passage of the blow pin away from the blow end;
   F) wherein when the blow pin is retracted the blow pin sterilization maintenance device maintains surface sterility of the pin and when the blow pin is extended into a parison held in a mold cavity sterile blow gas flowed into the parison from the source of sterile blow gas and through the blow passage blows the parison to form a sterile bottle and blow gas is exhausted from the bottle to the vacuum source through the exhaust passage without exhausting blow air through the blow passage to maintain sterility of the blow passage.

13. The assembly as in claim 12 wherein the blow pin sterilization maintenance device cooperates with the blow pin to define an annular gas chamber surrounding the sterile surface of the blow pin when the blow pin is retracted, an inlet port in the maintenance device leading to the gas chamber, and a second source of sterile gas connected to the inlet port, wherein sterile gas from said second source flows into the chamber and surrounds the sterile surface of the blow pin to maintain sterility of such surface.

14. The assembly of claim 13 including a first circumferential seal between the sterilization maintenance device and the blow pin away from the blow end of the blow pin and an annular mouth between such device and the blow pin adjacent the blow end of the blow pin, wherein sterile gas from said second source slows flows into the chamber, surrounds the blow pin and out of the chamber through said mouth.

15. The assembly of claim 14 wherein the blow pin is cylindrical, said blow end is blunt and said flow of sterile air from the second source along the blow pin is laminar and extends around the blow end to prevent contamination of the sterile surface.

16. The assembly as in claim 15 wherein the pressure of the sterile air from said second source is not greater than about one pound per square inch.

17. The assembly as in claim 14 wherein said circumferential seal includes a first circumferential portion mounted on the blow pin, a second circumferential portion mounted on the sterilization maintenance device and a flexible circumferential portion extending between said first and second portions.

18. The assembly as in claim 17 wherein said flexible portion comprises a diaphragm.

19. The assembly as in claim 18 wherein the diaphragm includes a circumferential bend.

20. The assembly as in claim 14 wherein the first circumferential seal comprises a first flexible diaphragm, and including a second circumferential seal extending between the blow pin and the sterilization maintenance device, said second circumferential seal including a second flexible diaphragm, said second seal spaced a distance along the blow pin from the first seal, an annular chamber between said seals, the blow pin and the sterilization maintenance device, and a vacuum port in the sterilization maintenance device opening into the annular chamber wherein a source of vacuum connected to the vacuum port maintains the annular chamber at subatmospheric pressure.

21. The method of blowing a sealed aseptic plastic bottle using a blow molding machine having a blow pin with a blow end, a sterile internal blow passage extending from a source of sterile blow gas through the blow pin to the end of the pin, a blow pin housing surrounding the blow pin and a blow pin drive to move the blow pin between extended and retracted positions, including the steps of:
  A) moving the blow pin to the retracted position to locate an end portion of the pin in the housing, flowing sterile gas at low pressure into a chamber between the pin and housing so that the sterile gas surrounds the pin and flows axially along the pin in laminar flow and over the end of the pin and the end of the blow passage to maintain sterility of the end of the pin and the passage;
  B) locating a closed blow mold with a parison captured in a blow cavity adjacent the blow pin;
  C) moving the blow pin outwardly from the housing to an extended position to locate the end of the blow pin in the mold in contact with the parison and with the end of the blow passage communicating with the interior of the parison while continuing to flow sterile air outwardly from the housing and along the blow pin to maintain sterility of the extended blow pin;
  D) maintaining the blow pin in contact with the parison while
    i) blowing sterile gas through the sterile blow passage, out the end of the passage and into the parison to blow the parison and form a sterile bottle;
    ii) removing blow gas from the interior of the blown bottle while maintaining the sterility of the blow passage to reduce the pressure within the bottle; and
    iii) sealing the bottle closed at a location below the blow pin after blow gas has been removed from the bottle;
  E) separating the blow pin from the bottle, moving the blow pin back to the retracted position in the housing and continuing to flow low pressure sterile gas along the pin in laminar flow and around the end of the pin to maintain the sterility of the pin; and
  F) opening the mold and removing the blown bottle.

22. The method of claim 21 including the step of:
  G) exhausting blow gas from the blown bottle through an exhaust passage in the blow pin separate from the blow air passage without exhausting gas through the blow passage.

23. The method of claim 21 including the step of:
  G) exhausting sufficient blow gas from the bottle to reduce the interior pressure of the bottle below atmospheric pressure and then sealing the bottle closed at subatmospheric pressure.

24. The method of claim 21 including the step of:
  H) flowing the sterile gas into the chamber at a pressure of about one pound per square inch or less.

25. The method of claim 21 including the step of:
  H) removing the bottle from the mold before sealing the bottle closed.

26. The method of claim 25 including the step of:
  I) maintaining the blow pin in contact with the parison until after the bottle is sealed closed.

27. A blow pin assembly for use in blow molding aseptic plastic bottles, the assembly including:
  A) an elongate blow pin having a blow end, the pin including a sterile internal blow air passage extending along the pin and having a blow mouth at the blow end of the pin;
  B) an annular blow pin housing surrounding the blow pin, the housing defining an upper opening and a lower mouth, and a sterile gas inlet port opening into a first annular chamber between the housing and the blow pin;
  C) a first circumferential seal adjacent the upper opening, said first seal extending between the housing and the blow pin when the blow pin is in a retracted position and the blow end of the pin is adjacent the housing, the surface of the pin below the first seal being sterile; and
  D) a drive for moving the blow pin between the retracted position and an extended position where the blow end of the pin is extended outwardly below the housing in position to blow a parison held in a closed mold below the housing,
  E) wherein when the blow pin is in the retracted position sterile gas flowed into the chamber through the sterile gas inlet port surrounds the blow pin, flows along the blow pin in laminar flow and across the blow end of the pin to shield the sterile pin from contamination by atmospheric air.

28. The assembly as in claim 27 including a circumferential recess in the blow pin housing extending around the blow pin, said first circumferential seal including a first circumferential portion in said recess.

29. The assembly as in claim 28 wherein said first circumferential seal includes a second portion located outwardly of said recess, said second portion engaging the blow pin.

30. The assembly as in claim 29 wherein said blow pin includes a tapered circumferential surface, said second portion of said first circumferential seal engaging such surface.

31. The assembly as in claim 27 wherein said first circumferential seal is flexible.

32. The assembly as in claim 27 wherein said blow pin housing includes first and second cylindrical members, and a second circumferential seal between such members.

33. The assembly as in claim 27 wherein the pressure on one side of said first circumferential seal is different than the pressure on the other side of said first circumferential seal.

34. The assembly as in claim 27 wherein the pressure in said blow pin housing is greater than pressure outside said blow pin housing.

* * * * *

UNITED STATES PATENT AND TRADEMARK OFFICE
CERTIFICATE OF CORRECTION

PATENT NO.    : 6,635,216 B2
DATED         : October 21, 2003
INVENTOR(S)   : Dundas et al.

It is certified that error appears in the above-identified patent and that said Letters Patent is hereby corrected as shown below:

Column 3,
Line 52, replace "unshaped" with -- u-shaped --.

Signed and Sealed this

First Day of June, 2004

JON W. DUDAS
*Acting Director of the United States Patent and Trademark Office*